United States Patent [19]

Potocky et al.

[11] Patent Number: 5,108,390

[45] Date of Patent: Apr. 28, 1992

[54] FLEXIBLE CRYOPROBE

[75] Inventors: Clifford E. Potocky, Shelton; Ronald M. Callanan; Raymond L. Goudreau, both of Seymour, all of Conn.

[73] Assignee: Frigitronics, Inc., Shelton, Conn.

[21] Appl. No.: 270,744

[22] Filed: Nov. 14, 1988

[51] Int. Cl.[5] ............................................. A61B 17/36
[52] U.S. Cl. ......................................................... 606/21
[58] Field of Search ................. 128/303.1, DIG. 27; 606/20, 21, 22-26

[56] References Cited

U.S. PATENT DOCUMENTS

| | | | |
|---|---|---|---|
| 3,823,718 | 7/1974 | Tromovitch | 128/303.1 |
| 3,859,986 | 1/1975 | Okada et al. | 128/7 |
| 3,910,277 | 10/1975 | Zimmer | 128/303.1 |
| 3,924,628 | 12/1975 | Droegemueller et al. | 128/303.1 |
| 4,018,227 | 4/1977 | Wallach | 128/303.1 |
| 4,275,734 | 6/1981 | Mitchiner | 128/303.1 |
| 4,278,090 | 7/1981 | Van Gerven | 128/303.1 |

Primary Examiner—Max Hindenburg
Attorney, Agent, or Firm—Parmelee, Bollinger & Bramblett

[57] ABSTRACT

Cryosurgery may be performed by a microinvasive technique employing a novel cryosurgical probe. It is very thin, very long, and highly flexible. These characteristics are achieved by a construction consisting of a tube within a tube with no intermediate supporting elements therebetween. The probe is capable of being passed through a blood vessel and into the heart without external guidance other than the blood vessel itself.

21 Claims, 4 Drawing Sheets

FLEXIBLE CRYOPROBE

TECHNICAL FIELD

This invention relates to the field of cryosurgical instruments. More particularly, it relates to such an instrument which is thin, flexible, and elongated, thereby allowing it to cool tissue within an animal body in the performance of microinvasive surgery. More specifically, the device of this invention lies in the field of instruments sufficiently thin and flexible to be threaded through a vein, artery, or similar structure of a living animal body.

BACKGROUND ART

Cryosurgery is a well established modality useful in the treatment of many conditions. Cooling and defrosting may be achieved by a variety of methods. Considering only probe-type instruments (as compared with external, usually dermatological, applications such as dry ice or liquid nitrogen applied directly to the skin), these may include: the introduction of a low boiling point refrigerant into the probe tip; gas expansion utilizing the Joule-Thompson effect; employing the latent heat of vaporization, as with Freon; precooled gases and liquids; or thermoelectric cooling.

It has also been proposed to provide flexible cryoprobes. One such probe is illustrated in U.S Pat. No. 3,859,986 of Okada, et al. Another is illustrated in U.S. Pat. No. 3,910,277 of Zimmer. However, neither of those devices would be suitable for introduction into, and subsequent passage through, a narrow curved passage such as a vein or artery. This is because they could not be made thin enough or flexible enough for such an application. For example, Okada, et al. employs a liquid refrigerant such as liquid nitrogen. The refrigerant is supplied through a flexible supply tube contained within a flexible outer tube. The inner tube must be thermally insulated from the outer tube. Accordingly, spacing ribs are required to separate them and permit the intervening space to be evacuated. Zimmer also employs liquid nitrogen in a tube-within-a-tube construction, but requires interlocking insulation rings, resulting in a relatively thick insulated tube.

U.S. Pat. No. 3,512,531 of Crump et al. is designed for insertion into an artery. However, it is employed for removing the diseased inner lining (or intima) which has been detached from the arterial wall. Accordingly, it is designed to be cooled along one side of its entire length, rather than at the end, in order to permit cryoadhesion along the length of the detached lining. Furthermore, although it is slightly flexible, it is not designed to be threaded through a blood vessel or similar passage to perform cryosurgery, for example within the heart.

Also relevant to the disclosure of this invention is the fact that the method of cooling and defrosting the cryoprobe is known. It comprises supplying a gas such as nitrous oxide ($N_2O$) or carbon dioxide ($CO_2$) from a room temperature bottle through a delivery system. The delivery system supplies the gas to the cryoprobe at either of a high pressure or a low pressure. When supplied at a high pressure, the gas expands through a restricted orifice in the freeze tip and cools by the Joule-Thompson effect. When supplied at a low pressure, the warm gas merely floods the tip and thaws it.

DISCLOSURE OF INVENTION

The invention comprises a very thin, very long, and very flexible exhaust tube capable of being threaded through a vein or artery for a substantial distance. The distal end of this exhaust tube is closed by a "freeze" tip having high thermal conductivity. An even smaller and equally flexible supply tube is contained within the exhaust tube and terminates at a small nozzle within, and adjacent the end of, the freeze tip. The composite tube may be snaked through a vein or artery from an incision therein until the freeze tip is positioned adjacent a region of, for example, the heart to be treated. A gas, such as nitrous oxide, from a high pressure source is then passed through the inner tube and expands from the nozzle at its end. This cools the tip by the well known Joule-Thompson effect. When sufficient cooling or freezing has taken place, the input switches to a low pressure gas supply. The low pressure, substantially room temperature, gas simply floods the entire tube and tip to warm, and thereby defrost, the tip to reverse cryoadhesion and permit the probe to be withdrawn. As explained above, this method of cooling and defrosting a cryosurgical instrument is known in the art.

BEST MODE FOR CARRYING OUT THE INVENTION

Figure 1:
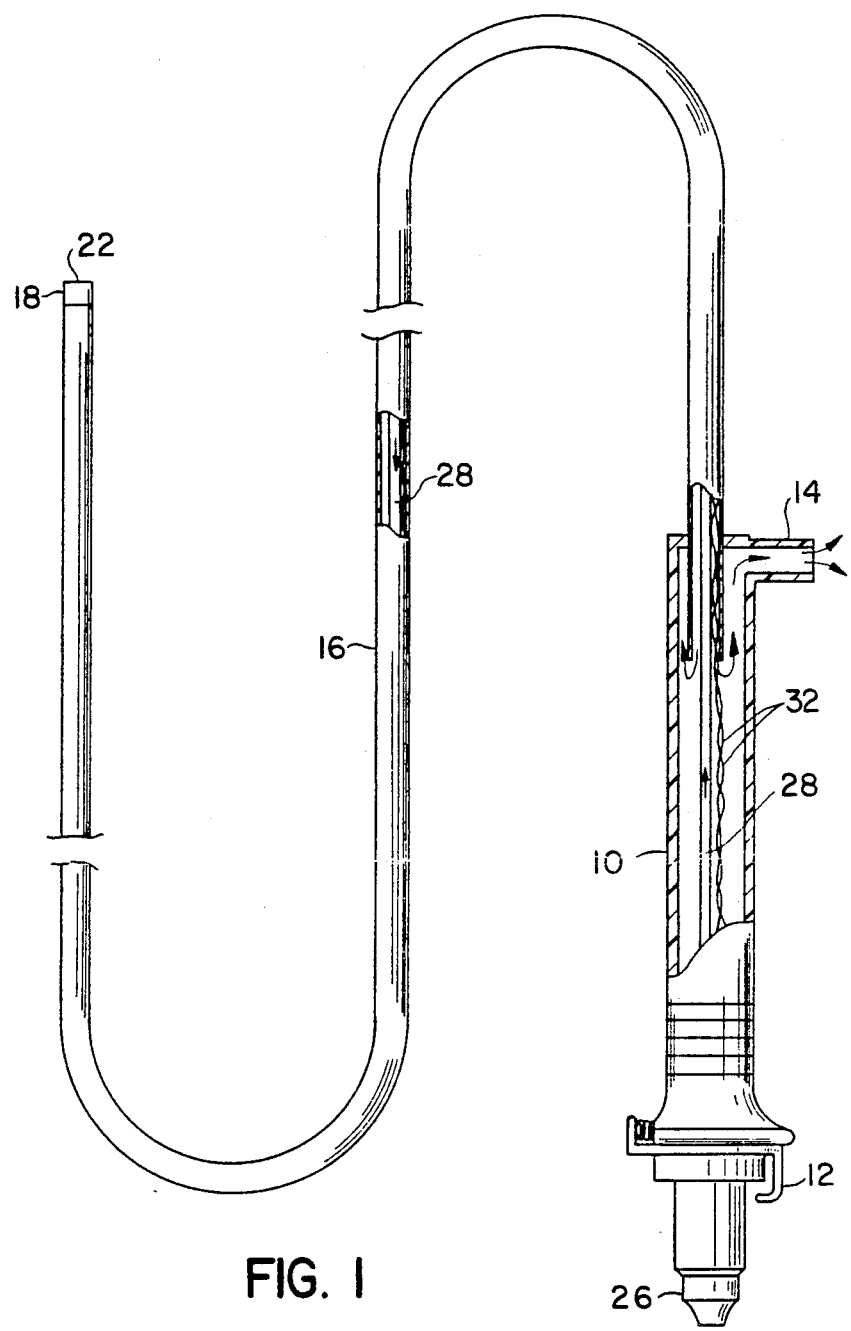
FIG. 1 is an elevational view, in partial cross-section, of a cryosurgical probe of the present invention.

With particular reference to FIG. 1, there is illustrated a cryosurgical probe in accordance with the present invention. It includes a plug 10 of conventional construction, having a spring-loaded latch 12 for connection to the gas supply port of a conventional gas delivery console (not shown). The plug 10 is substantially cylindrical as shown and, at its outer end, includes a radial exhaust outlet 14 extending into its interior.

Secured in the end of the plug 10 by any suitable means such as an epoxy or a mechanical seal is the proximal end of a very long, very thin, and very flexible exhaust line 16. For use as a cardiac probe, the exhaust line 16 must have an extremely high length to diameter ratio, on the order of at least 100:1. Also, it must, of course, be compatible with the inner lining of the blood vessels and with other tissues to be encountered. In one actual embodiment of the invention, this line had a diameter of 0.125 inch (3.2 mm) and a length of six feet (1.85 m). The inside diameter was 0.072 inch (1.8 mm). The length to diameter ratio was approximately 575. It was made of nylon.

Figure 2:
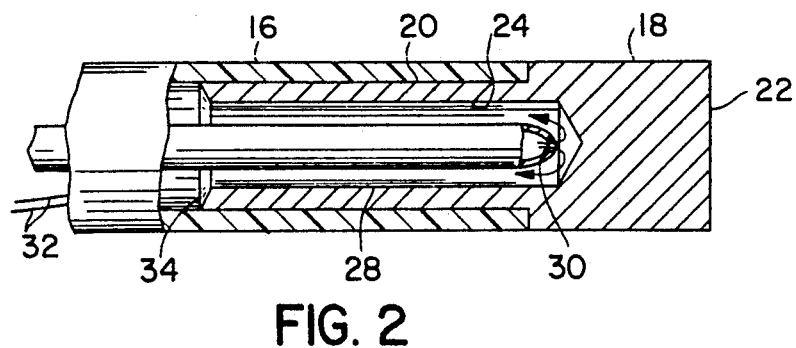
FIG. 2 is an enlarged cross-section of the operating tip of the probe of FIG. 1.

The distal end of the exhaust tube 16 is closed by a freeze tip 18 of a high thermal conductivity material. In the exemplary embodiment, this tip was of silver. It has a shank 20 (FIG. 2) having an outside diameter corresponding to the inside diameter of the exhaust line 16 so that it fits within the end of the exhaust line 16. It is bonded to the exhaust line by any suitable method such as mechanical attachment, ultrasonic welding, or by a suitable adhesive such as an epoxy. As will be apparent from FIG. 2, the outer circumferences of the freeze tip 18, and the exhaust line 16 are the same, so as to form a smooth continuous surface. In the embodiment shown in FIG. 2, the freeze tip 18 has a cylindrical shape with a planar end face 22. However, this shape could be varied for specific applications. The freeze tip 18 is drilled to form a chamber 24 extending into o it from the exhaust line 16. In the embodiment of the example, this chamber had a diameter of 0.050 inch (1.3 mm). The length of the chamber 24 was 0.23 inch (6 mm) and the exposed length of the freeze tip 18 was 0.12 inch (3 mm).

Starting at the input end 26 of the plug 10 is a thin walled stainless steel delivery line 28. When the plug 10 is connected in the delivery port of the gas supply console, gas enters the proximal end of the delivery tube 28. In the exemplary embodiment described herein, the delivery line 28 had an outside diameter of 0.032 inch (0.8 mm) and a wall thickness of approximately 0.003 inch (0.05 mm). The delivery line 28 extends through the exhaust line 16 and into the chamber 24 of the freeze tip 18. The distal end of the delivery line 28 is rolled down to form an orifice 30. In the exemplary embodiment the diameter of the orifice was 0.007 inch (0.18 mm) and was located approximately 0.030 inch (0.75 mm) from the end of the chamber 24.

Extending through the length of the exhaust line 16 are a pair of thin thermocouple wires 32 which form a thermocouple junction 34 on the inside end of the freeze tip 18. The electrical connection of the thermocouple wires 32 to a temperature gauge on the console can be made in any suitable manner such as, for example, a connector such as shown and described in U.S. Pat. No. 3,629,786 of Reynolds, et al.

Figure 3:
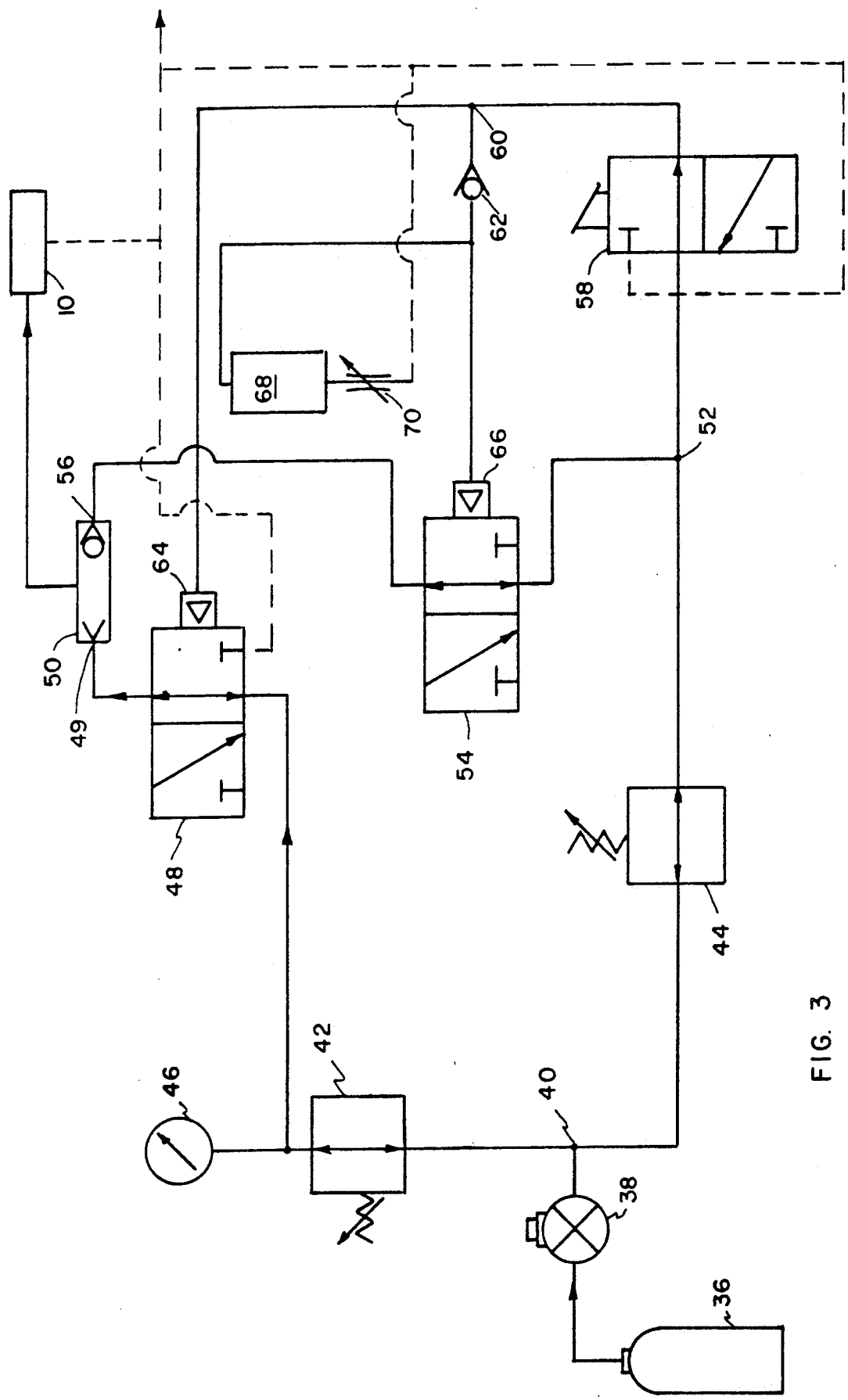
FIG. 3 is a schematic diagram of the cryoprobe gas supply in the freezing mode.

FIG. 3 illustrates the means by which a suitable gas such as nitrous oxide ($N_2O$) or carbon dioxide ($CO_2$) is supplied from a source such as a bottle 36 to effect freezing or cooling of the freeze tip 18. In this diagram, solid lines denote supply gas flow and dotted lines denote exhaust gas flow. Gas passes into the console through an on/off valve 38. From a tee 40, gas is supplied to a high pressure regulator 42 and to a low pressure regulator 44. The output from the high pressure regulator 42 is connected to a pressure gauge 46 and to an input port of a sliding three-way valve 48. The output from the three-way valve 48 is connected to a first input port 49 of a shuttle valve 50. An output port of the shuttle valve 50 is connected to the probe plug 10 which, in turn, is connected to the cryoprobe as previously described.

The low pressure regulator 44 has its output connected through a tee 52 to a sliding three-way valve 54 and to a foot "switch" 58. The output port of three-way valve 54 is connected to a second input port 56 on the shuttle valve 50.

The output from foot switch 58 is connected through a tee 60 to a check valve 62 and to the control port 64 of the three-way valve 48. The output from the check valve 62 is applied to the control port 66 of the three-way valve 54. A ballast chamber 68, having a variable resistor 70 to exhaust, is connected to this line.

When the valves are positioned as illustrated in FIG. 3 the probe is in a freezing mode. Gas from the bottle 36 enters the system through valve 38 and passes through low pressure regulator 44 which drops its pressure to 85-90 psi. This relatively low pressure gas passes through the foot switch 58 and is applied to the control port 64 of the three-way valve 48 forcing it to the left, or illustrated, position in which it connects the high pressure output of regulator 42 to the first input port 49 of shuttle valve 50. The high pressure regulator 42 controls the gas pressure over a wide range. This gas, entering the first input port 49 of the shuttle valve 50 actuates the shuttle valve due to pressure differential so as to close the second input port 56. The high pressure gas flows from the outlet of the shuttle valve into the probe plug 10 through the delivery line 28 and expands through the orifice 30 in the freeze tip 18. The expansion of the gas through this orifice causes it to cool and rapidly lowers the temperature of the freeze tip 18 to freezing levels. The expanded, and now low pressure, exhaust gas travels back along the outside of the delivery tube 28 within the exhaust line 16 and exhausts from the exhaust outlet 14 in the probe plug 10.

Figure 4:
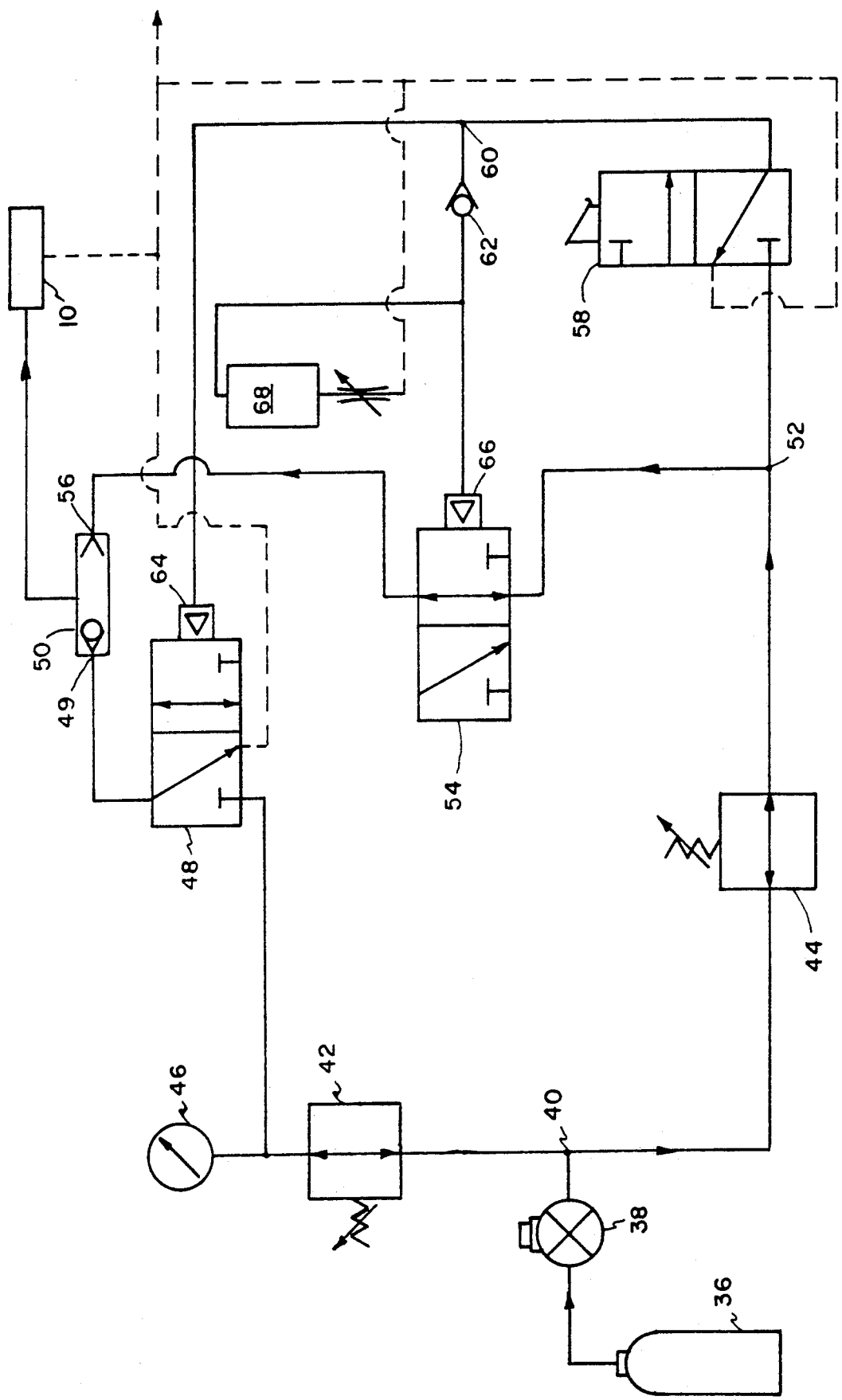
FIG. 4 is a diagram similar to that of FIG. 3 showing the gas supply in the defrost mode.

When freezing or cooling has proceeded to the desired extent, the surgeon releases the foot switch 58 into the position illustrated in FIG. 4. He thereby disconnects the low pressure gas supply from the control port 64 of the three-way valve 48, causing it to revert to the position illustrated where it cuts off the high pressure gas supply to the shuttle valve 50. The first input port 49 of shuttle valve 50 is thereby connected to exhaust and the low pressure gas entering the second input port 56 actuates the shuttle valve, permitting low pressure gas to flow to probe plug 10. This low pressure gas flows through the delivery line 28 and into the freeze tip 18. However, at this low pressure there is minimal, Joule-Thompson expansion through the orifice 30. Rather, the warm gas floods the probe tip 18, warming and rapidly thawing it so that it is readily removable from any tissue to which it has adhered. This is much safer than the system employed in some cryosurgical probes utilizing the Joule-Thompson effect wherein defrosting is achieved by pressurizing the exhaust line of the probe by blocking the exhaust.

FIGS. 3 and 4 illustrate the gas supply system in only the freeze and defrost modes. It will also be obvious that a third mode exists, which has not been illustrated, which is simply a standby condition.

The cryosurgical probe of this invention can be utilized in many procedures, but is particularly valuable for cardiovascular surgery. Use of this probe will eliminate the need for open heart open chest surgery on many arrhythmia patients where partial or complete heart block is required. It may be supplied to the surgeon either as a reusable, sterilizable device, or as a disposable single-use device.

Figure 5:
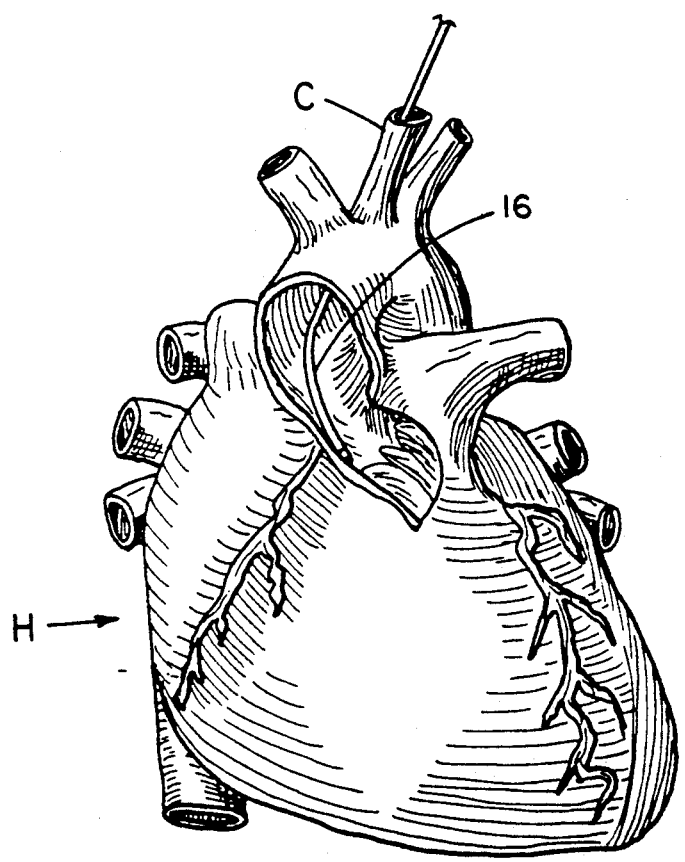
FIG. 5 is an illustration showing the operation of the probe of the invention in treating a human heart.

One method of utilizing the probe of the invention would be to supply it in the operating room in a sterile package as a disposable single-use device. The package would then be opened, the probe connected to the console and tested in sterile water to insure proper operation and that it is leak free. An incision would then be made, for example in the femoral artery in the groin. The probe would be inserted through this incision and snaked through the artery in the same fashion as a balloon catheter in an angioplasty procedure. The probe would be advanced through the selected vessel under the guidance of X-ray fluoroscopy, for example, to the area to be treated, such as the atrioventricular (AV) node, the sinoatrial (SA) node, the His bundle, etc. FIG. 5, for example illustrates the probe exhaust line 16 positioned within a heart H by entrance through the left common carotid artery C. The tissue to be treated can then be cooled or destroyed by freezing.

A "reversible freeze" is possible with the probe of this invention. To accomplish this, the freeze tip 18 is maintained at a temperature between about 0° C. and −20° C. The cardiovascular surgeon can utilize this technique to insure the correct location of the probe. When the tissue is cooled but not irreversibly destroyed, electrical conduction through that region will stop, but will return to normal when warmed. In this manner the area to be treated can be verified or mapped. When the flexible probe tip is in contact with the target area, the area may be frozen to maximum freeze temperature to permanently affect electrical conduction. The probe can then be defrosted, relocated to another target area or removed from the vein or artery, the incision then being closed to complete the procedure.

It is believed that the many advantages of this invention will now be apparent to those skilled in the art. It will also be apparent that a number of variations and modifications may be made therein without departing from its spirit and scope. Accordingly, the foregoing description is to be construed as illustrative only, rather than limiting. This invention is limited only by the scope of following claims.

We claim:

1. Apparatus for cryosurgically treating tissue within a living body which comprises:
    an elongated, thin, first tube adapted to be inserted through a blood vessel of the body being treated and highly flexible to follow the natural contours of the blood vessel, said first tube having a distal end defining a first orifice and a proximal end;
    a cooling tip carried by the distal end of said first tube, said tip being formed of a material having relatively high thermal conductivity and having an outer surface contactable with the tissue to be treated;
    an elongated, thin, second tube associated with and parallel to said first tube, said second tube being highly flexible to conform to and follow said first tube through said blood vessel and having a distal end defining a second orifice adjacent said cooling tip and a proximal end;
    means for selectively injecting a fluid refrigerating medium into the proximal end of one of said first and second tubes for passage out of its associated orifice to refrigerate said cooling tip; and
    means for exhausting said refrigerating medium from the other of said first and second tubes at a distance from said treated tissue.

2. The apparatus of claim 1 wherein each of said first and second tubes has a length to diameter ratio of at least 100:1.

3. The apparatus of claim 2 wherein said refrigerating medium is a gas and wherein refrigeration is by Joule-Thompson cooling upon expansion from said orifice.

4. The apparatus of claim 3 wherein said gas is $N_2O$.

5. The apparatus of claim 3 wherein said bas is $CO_2$.

6. The apparatus of claim 2 wherein said second tube is contained within said first tube.

7. The apparatus of claim 6 wherein said cooling tip is hollow and secured to the first orifice of said first tube.

8. The apparatus of claim 7 wherein said second orifice is of smaller diameter than said second tube and is positioned within said hollow cooling tip.

9. The apparatus of claim 8 wherein said refrigerating medium is a gas and refrigeration is by Joule-Thompson cooling upon expansion from said second orifice.

10. The apparatus of claim 9 wherein said gas is $N_2O$.

11. The apparatus of claim 9 wherein said gas is $CO_2$.

12. The apparatus of claim 1 wherein said fluid refrigerating medium is a gas and wherein refrigeration is by Joule-Thompson cooling upon its expansion from said orifice.

13. The apparatus of claim 12 wherein said gas injecting means selectively injects gas at either of:
    a) a high pressure to initiate cooling of said cooling tip; or
    b) a low pressure to initiate warming of said cooling tip.

14. The apparatus of claim 12 wherein said gas is $N_2O$.

15. The apparatus of claim 12 wherein said gas is $CO_2$.

16. The method of cooling a selected region of tissue adjacent a blood vessel within a living body which comprises:
    inserting into said blood vessel an elongated, thin, highly flexible probe having a distal end comprising a cooling tip formed of a material having relatively high thermal conductivity and a proximal end, the proximal end remaining outside said body;
    continuing the insertion of said probe whereby it is guided through said blood vessel substantially solely by the blood vessel itself to position its cooling tip in contact with the selected tissue region;
    cooling substantially only the cooling tip of the probe to cool the selected tissue region to a desired temperature;
    terminating the cooling of the cooling tip of the probe; and
    withdrawing the probe from said blood vessel.

17. The method of claim 16 wherein said elongated probe comprises an outer exhaust tube and an inner delivery tube terminating at an orifice within said hollow cooling tip and wherein cooling is achieved by the step of injecting a refrigerating medium through said delivery tube orifice into said cooling tip and exhausting said refrigerating medium from said cooing tip through said exhaust tube.

18. The method of claim 17 wherein said refrigerating medium is a gas and wherein cooling results from Joule-Thompson expansion of said gas within said hollow cooling tip.

19. The method of claim 18 wherein cooling is terminated by lowering the pressure of the gas to minimize the Joule-Thompson expansion and flood the hollow cooling tip with relatively warm gas.

20. The method of claim 19 wherein said gas is $N_2O$.

21. The method of claim 19 wherein said gas is $CO_2$.

* * * * *